(12) United States Patent
Fitzgerald et al.

(10) Patent No.: US 6,232,090 B1
(45) Date of Patent: May 15, 2001

(54) DRIED TETRAMETHOXYSILANE SOL-GEL CONTAINING A LEACHABLE REAGENT

(75) Inventors: Stephen Peter Fitzgerald; John Victor Lamont; Robert Ivan McConnell, all of Co. Antrim (GB)

(73) Assignee: Randox Laboratories Ltd., Crumlin (GB)

( * ) Notice: Subject to any disclaimer, the term of this patent is extended or adjusted under 35 U.S.C. 154(b) by 0 days.

(21) Appl. No.: 09/192,280

(22) Filed: Nov. 16, 1998

(30) Foreign Application Priority Data

Nov. 19, 1997 (EP) .................................... 97309322

(51) Int. Cl.[7] .............................. C12Q 1/00; C12Q 1/28; C12N 11/00; C12N 11/14; C12N 11/04
(52) U.S. Cl. ................................ 435/28; 435/4; 435/174; 435/176; 435/182
(58) Field of Search ........................... 435/4, 8, 28, 174, 435/176, 182

(56) References Cited

U.S. PATENT DOCUMENTS

| 5,200,334 | 4/1993 | Dunn et al. | 435/182 |
| 5,608,006 | 3/1997 | Myerson | 525/54.1 |

FOREIGN PATENT DOCUMENTS

| 0 434 317 A1 | 6/1991 | (EP) . |
| 0 439 318 A2 | 7/1991 | (EP) . |

OTHER PUBLICATIONS

Braun, S. et al., "Design and Properties of Enzymes Immobiolized in Sol–Gel Glass Matrices," Biotechnology: Bridging Research and Applications, Kluwer Academic, Boston, 1991, pp. 205–218.

Piechota, I. et al., "Untersuchungen Zur Synthese Loslicher Glaser Nach Dem Sol–Gel Verfahren Und Zur Kontrollierten Freisetzung Von Fluorescein–Natrium," Acta Pharm. Technol., vol. 34, 1988, p. 27s.

Coche–Guerente, L. et al., "Sol–Gel Derived Composite Materials for the Construction of Oxidase/Peroxidase Mediatorless Biosensors," Chem. Mater., vol. 9, 1997, pp. 1348–1352.

*Primary Examiner*—David M. Naff
(74) *Attorney, Agent, or Firm*—Oliff & Berridge, PLC

(57) ABSTRACT

First and second reactants that give a signal when mixed in the presence of an analyte in a liquid sample, are separately contained in sol-gels that release the reactants in the presence of the liquid. For example, when the first and second reactants respectively comprise an oxidant and a reductant, and the reaction provides a detectable signal, the system can be used to detect the presence of contaminants in a water sample. The sol-gel may be obtained by reaction of water with, per part by volume thereof, at least 2 parts of a metal alkoxide, and drying the resultant gel.

18 Claims, 3 Drawing Sheets

Figure 7:
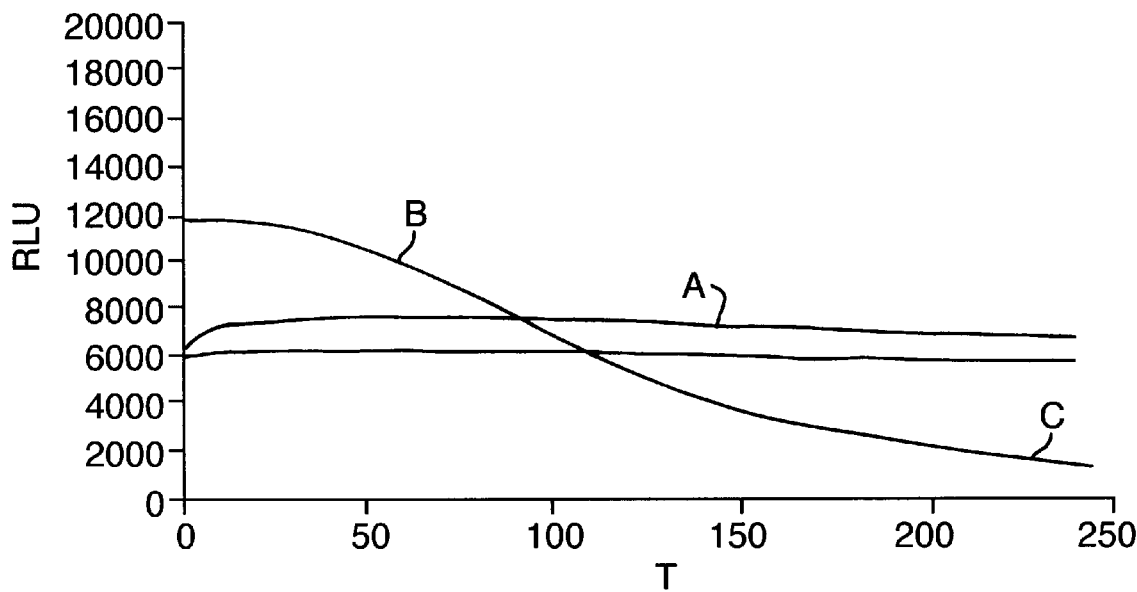

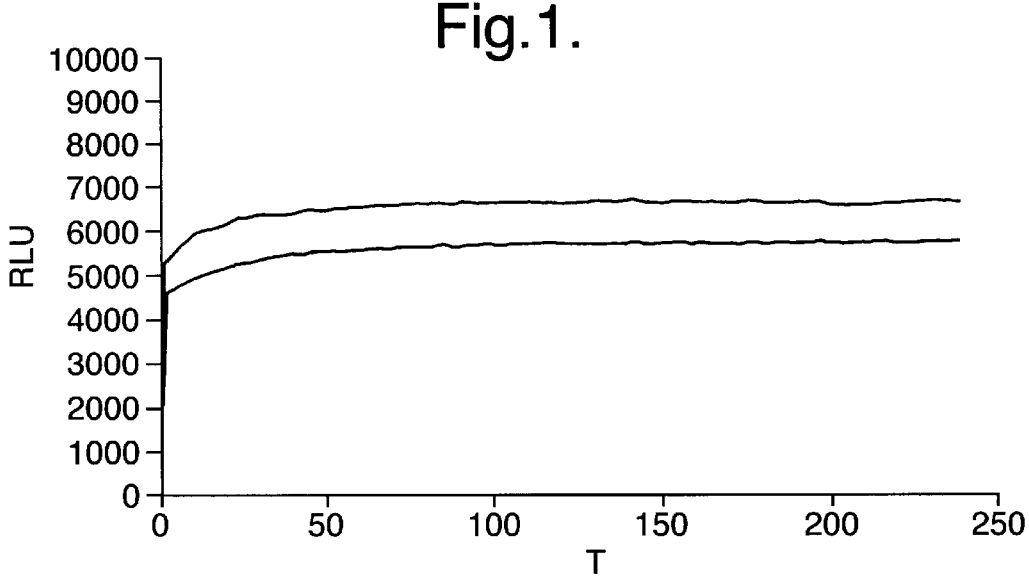
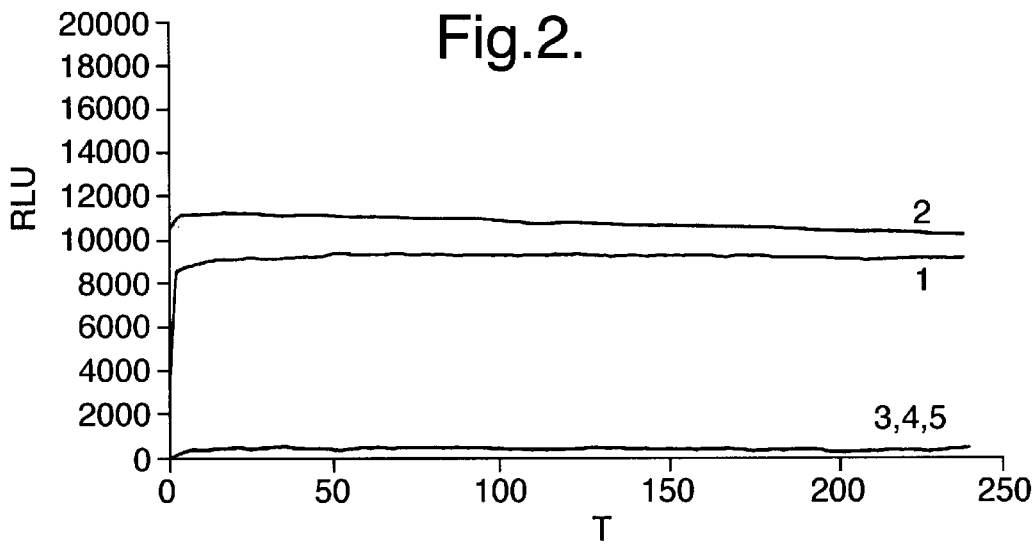
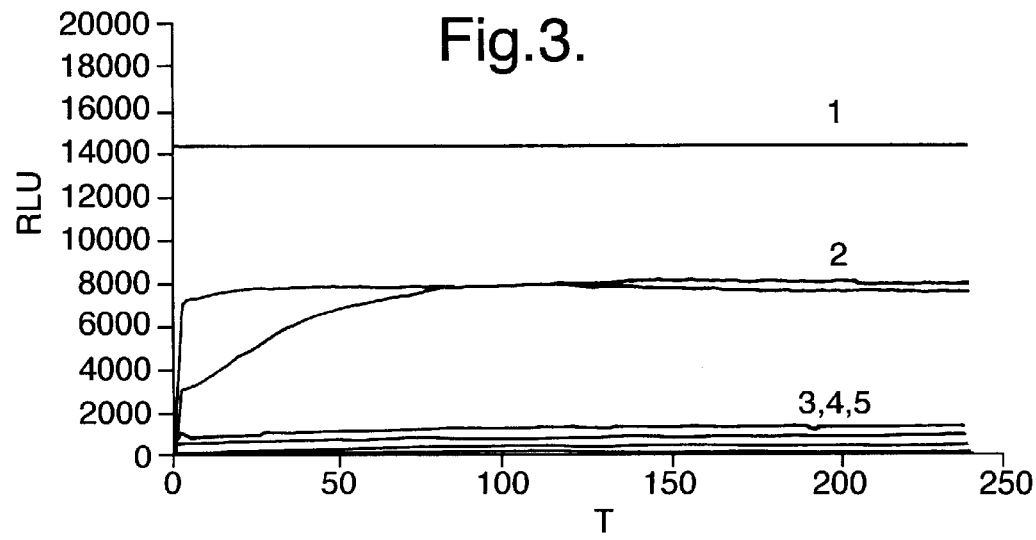

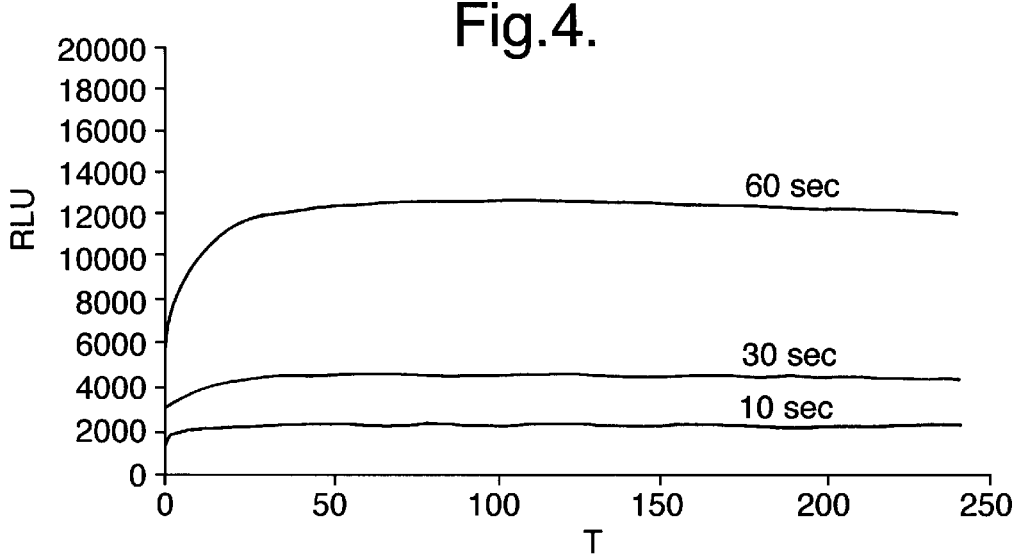
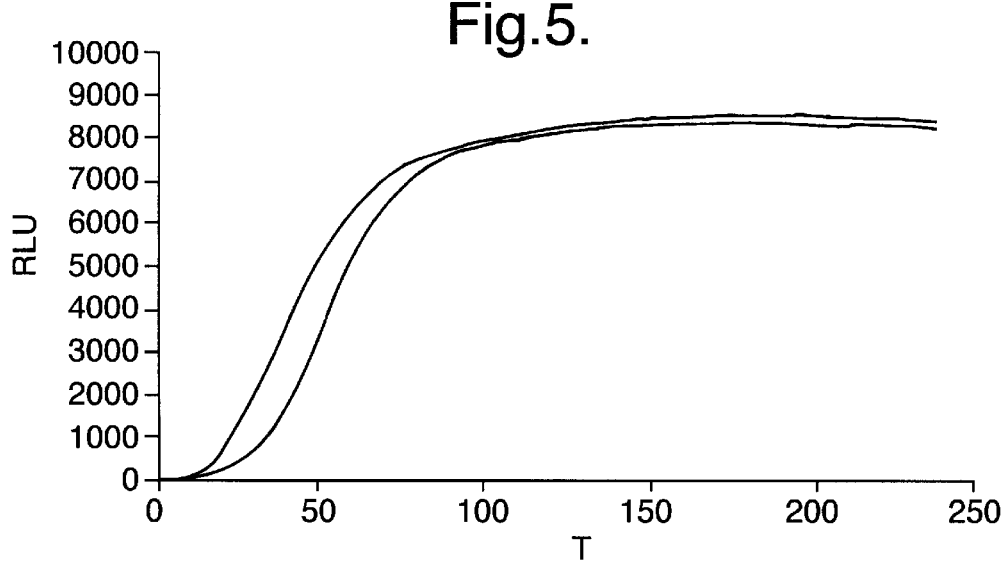
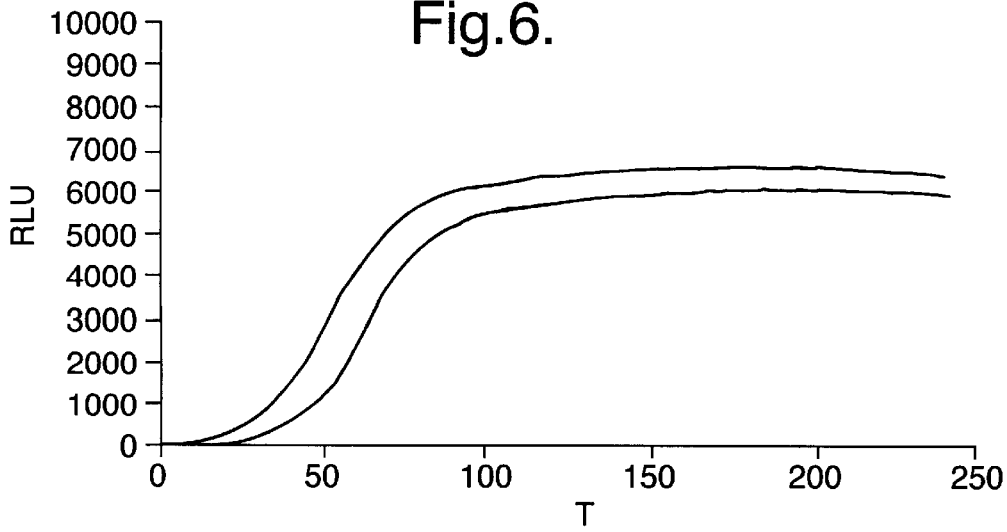

DRIED TETRAMETHOXYSILANE SOL-GEL CONTAINING A LEACHABLE REAGENT

FIELD OF THE INVENTION

This invention relates to sol-gels and their use in water quality assays.

BACKGROUND OF THE INVENTION

Water courses may be contaminated with substances such as sewage, heavy metals, pesticides containing organic residues etc. Such substances act as free radical scavengers. They can therefore be assayed using a light-producing free radical reaction; the light emission is reduced or inhibited to a degree proportional to the amount of contaminant present, when compared to a distilled water control.

One such test, available under the trade name Aquanox, from Randox Laboratories Limited, involves a free radical reaction between a hydrogen acceptor (oxidant) and a hydrogen donor (luminol) in the presence of an enhancer. This reaction is catalysed by horseradish peroxidase (HRP) and results in light emission at a constant rate.

At present, in order for the Aquanox assay to be performed, a vial of freeze-dried signal reagent (containing luminol, enhancer and oxidant) is reconstituted with 5 ml borate buffer (pH 8.5), and then 100 µl of this solution, 20 µl enzyme reagent plus 1 ml water sample are added to a disposable cuvette. The reaction is started by the addition of the enzyme reagent. The separate additions of signal reagent, enzyme and sample to the cuvette have proved difficult for some users when undertaken in the field, especially to less technically skilled personnel.

Sol-gels are known. The sol-gel process involves the mixing of metal alkoxides, e.g. TMOS, i.e. tetramethoxysilane, in solution with water and a catalyst, at room temperature. In this process, a complex series of hydrolysis and polymerisation reactions occurs. The initially fluid solution becomes viscous as polymerisation proceeds, until a gel is formed. The gel is then dried, during which process liquid is expelled, causing substantial volume shrinkage of the gel, leaving a dry porous solid. The pore networks formed in dried gels do not scatter visible radiation and are therefore optically transparent.

Molecules added in the sol-gel process become entrapped in the growing covalent network. For example, Piechota and Sueverkruep, Acta. Pharm. Technol. 34:27s (1988), discloses sol-gels of unspecified composition, containing fluorescein. The marker was released at an essentially constant rate over 5–8 hours, and the rate varied with increasing phosphate content.

Further, EP-A-0439318 discloses a reagent trapped in a sol-gel glass, with the intention that a desired reaction with an analyte should occur within the pores of the network. The Examples disclose TMOS:solvent ratios of approx. 2:3 for sol-gel shapes and 1:8 for thin films.

SUMMARY OF THE INVENTION

The present invention is based on the discovery that, by increasing the TMOS:solvent ratio, sol-gels can be produced that satisfactorily retain a reactant therein, but which can readily be leached out in the presence of water. This is particularly suitable when it is desired to supply reactants to a user in a mixture, but physically separate, until use.

According to one aspect of the present invention, a sol-gel containing a reactant is obtainable by reaction of water with, per part thereof, at least 2 parts of a metal alkoxide such as TMOS, and drying the resultant gel.

According to a second aspect of the invention, for a combination of first and second reactants that give a signal when mixed in the presence of an analyte in a liquid sample, the reactants are separately contained in sol-gels that release the reactants in the presence of the liquid.

DESCRIPTION OF THE INVENTION

By virtue of the invention, the reactants that are required for use in, say, the Aquanox system can be supplied in dry/solid form, e.g. as a dry mixture of any desired shape, films, pellets or powder. For the purpose of this specification, the term "reactant" is used to describe one or more components. If two or more components are contained in one sol-gel, they should not be mutually reactive.

The reactants that may be used in the present invention are not limited. Examples include organic and inorganic ligands, antibodies, enzymes, oxidising and reducing agents, reaction enhancers, signal-generators and labels. Similarly, the components of the sol-gels are not limited, although TMOS is preferred. The preferred alkoxide:water ratio (by volume) is 2.5:1 to 5:1.

The invention will now be described by way of example only with reference to the components used in the Aquanox system. Thus, the first reactant comprises at least luminol as hydrogen donor (reductant) and the second reactant comprises sodium perborate as hydrogen acceptor (oxidant). The first reactant may additionally comprise horseradish peroxidase, and either reactant may additionally comprise enhancer (p-iodophenol), or either or each of these additional components may be contained in further sol-gels. For use in an Aquanox cuvette, these four components may be provided in dried pellet form; no interaction occurs until the water sample is added. However, once water is added, the gels are such that sufficient of the components quickly leach out of their respective sol-gel pellets, and react together, free in solution.

The following Examples illustrate the invention, or are for the purposes of comparison. More specifically, Examples 1 and 2 (TMOS:water ratio is 5:1 or 5:2) are illustrative; Examples 3 to 5 (TMOS:water ratio is 3:2, 1:1 or 1:2) are comparative.

In the Examples, TMOS is tetramethoxysilane/tetramethyl orthosilicate. Citrate phosphate buffer, pH 6.0, comprises the acid and $Na_2HPO_4$. Borate buffer, pH 8.5, comprises sodium tetraborate, N-methylisothiazolone and 2-chloroacetamide.

Preparation of Sol-Gels

1. Sol-gel pellets of total volume 200 µl were prepared in the wells of Nunc clear microtitre plates, by the following method:
   (i) HRP-pellets—into each well was pipetted 100 µl pH 6.0 citrate phosphate buffer which contained the following:
      (a) 1, 1.5 or 2 mg/ml HRP only
      (b) 1, 1.5 or 2 mg/ml HRP plus 1% polyvinyl alcohol (9000–10,000 mw) or 1% polysucrose (400,000 mw).
   (ii) Luminol/p-iodophenol pellets—into each well was pipetted 100 µl 8.0 borate buffer which contained 12 mM luminol and 1.2 mM p-iodophenol.
   (iii) Sodium perborate pellets—into each well was pipetted 100 µl pH 8.0 borate buffer which contained 50 mM or 100 mM sodium perborate.
2. Into each well was pipetted 100 µl TMOS sol containing, per ml, 30 µl 40 mM HCl and one of the following ratios of TMOS:H$_2$O—5:1, 5:2, 3:2, 1:1 and 1:2. The TMOS sols were prepared in brown glass vials and the reagents were mixed by vortexing for approximately 30 seconds, until the solution was clear and the initial two layers had disappeared. After vortexing, the vials were cooled to room temperature before the sol was added to the wells.

Once the 100 μl TMOS sol was added to the wells, the concentration of reagents was therefore half the value initially present in the well, i.e. 0.5, 0.75 or 1 mg/ml HRP or 6 mM luminol/0.6 mM iodophenol or 25 and 50 mM sodium perborate.

3. After gelling occurred (within minutes), the HRP-containing gels were dried at ambient room temperature by placing the microtitre plates in a desiccator containing silica gel, in the dark, until no further weight loss was recorded. Those gels containing the signal reagent components were dried in vacuo in the desiccator, at ambient room temperature, in the dark.

Assay of Sol-Gels

The control Aquanox assay contained 1 ml deionised water, 100 μl reconstituted signal reagent and 20 μl enzyme reagent. The sol-gel pellets were assayed as follows:

(i) 1×HRP pellet+1 ml deionised water+100 μl reconstituted signal reagent.
(ii) 1×HRP pellet+1×luminol/iodophenol pellet+1× sodium perborate pellet+1 ml deionised water.
(iii) 1×luminol/iodophenol pellet+1×sodium perborate pellet+20 μl enzyme reagent.
(iv) The wash-water from the above pellets+the corresponding liquid enzyme or reconstituted signal reagent. To obtain this wash-water, 1 ml of deionised water was added to a pellet in a cuvette (or 2 pellets if luminol/iodophenol+perborate pellets were used) and the cuvette left for a specific length of time, up to 4 mins. The water was then pipetted off and assayed.

Results

The accompanying figures are plots of RLU (relative light units) against T (time; sec). These results are representative examples of the assays performed using a mixture of the individual dried sol-gel pellets and current liquid Aquanox components. An Aquanox (liquid constituents) control graph is included, for comparison.

FIG. 1 is the Aquanox control graph, obtained using 1 ml deionised water, 100 μl reconstituted signal reagent and 20 μl enzyme reagent.

FIG. 2 illustrates results obtained for each of Examples 1 to 5, and the effect of altering the TMOS:H$_2$O ratio (in the 100 μl TMOS sol added to each well). The 1 ml wash-water from soaking pellets containing 1 mg/ml HRP was assayed with liquid signal reagent for each of the TMOS:water ratios, therefore indicating the amount of HRP leaching. The results are given in Table 1.

TABLE 1

| Example | TMOS:H$_2$O | 2 min RLU | 4 min RLU | Integrated RLU |
| --- | --- | --- | --- | --- |
| 1 | 5:1 | 9490 | 9352 | 2251534 |
| 2 | 5:2 | 10977 | >9999 | 2633369 |
| 3 | 3:2 | 142 | 72 | 18976 |
| 4 | 1:1 | 581 | 616 | 137552 |

TABLE 1-continued

| Example | TMOS:H$_2$O | 2 min RLU | 4 min RLU | Integrated RLU |
| --- | --- | --- | --- | --- |
| 5 | 1:2 | 100 | 88 | 21974 |

FIG. 3 again illustrates the effect of altering the TMOS:H$_2$O ratio (in the 100 μl TMOS sol added to each well). The HRP-pellets (1 mg/ml) were assayed with 100 μl signal reagent. The results are given in Table 2.

TABLE 2

| Example | TMOS:H$_2$O | 2 min RLU | 4 min RLU | Integrated RLU |
| --- | --- | --- | --- | --- |
| 1 | 5:1 | 14320 | >9999 | 3451516 |
|   |     | 14356 | >9999 | 3451516 |
| 2 | 5:2 | 7810 | 7571 | 1856696 |
|   |     | 8193 | 7901 | 1758114 |
| 3 | 3:2 | 207 | 200 | 44923 |
|   |     | 420 | 396 | 84010 |
| 4 | 1:2 | 942 | 930 | 212148 |
|   |     | 451 | 431 | 98963 |
| 5 | 1:1 | 681 | 789 | 159774 |
|   |     | 365 | 353 | 79096 |

FIG. 4 illustrates the activity obtained from timed washings of signal reagent sol-gel pellets (6 mM/0.6 mM luminol/liodophenol+25 mM sodium perborate). These washing were assayed with 20 μl enzyme reagent. The results are given in Table 3.

TABLE 3

| Wash (sec) | 2 min RLU | 4 min RLU | Integrated RLU |
| --- | --- | --- | --- |
| 60 | 12643 | 9999 | 2946658 |
| 30 | 4690 | 4431 | 1083869 |
| 10 | 2764 | 2760 | 639809 |

FIGS. 5 and 6 illustrate the activity obtained with signal sol-gel pellets assayed with 5 μl enzyme reagent (6/0.6 mM luminol/iodophenol+25 or 50 mM sodium perborate). The corresponding figures are given in Tables 4 (for 50 mM) and 5 (for 25 mM).

TABLE 4

| 2 min RLU | 4 min RLU | Integrated RLU |
| --- | --- | --- |
| 8235 | 8327 | 1620539 |
| 8115 | 8185 | 1520189 |

TABLE 5

| 2 min RLU | 4 min RLU | Integrated RLU |
| --- | --- | --- |
| 6468 | 6442 | 1220093 |
| 5813 | 5956 | 1051484 |

Figure 8:
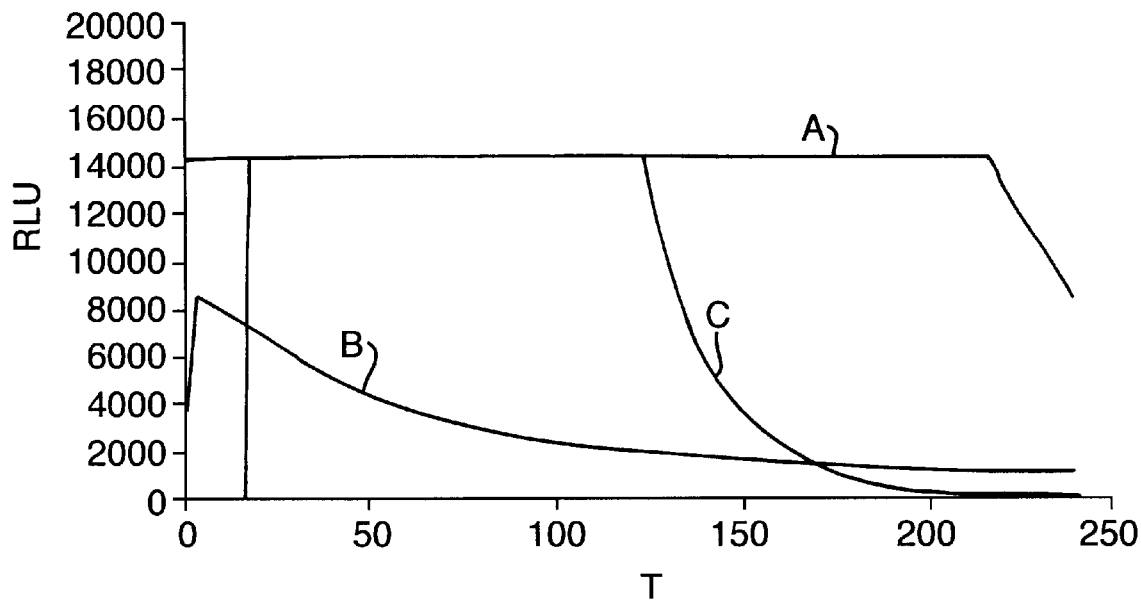

FIGS. 7 and 8 illustrate the results obtained from HRP-doped pellets containing 0.75 mg/ml and 1 mg/ml, respectively, of the additives polysucrose (mw 400,000) or polyvinyl alcohol (mw 9000–10,000), assayed with liquid signal reagent (A) or signal sol-gel pellets (B). Assays C uses the wash of HRP sol-gel and liquid signal. The corresponding figures are given in Tables 6 (0.75 mg/ml with PVA) and 7 (1 mg/ml with polysucrose).

TABLE 6

| Assay | 2 min RLU | 4 min RLU | Integrated RLU |
| --- | --- | --- | --- |
| A | 7521 | 7428 | 1799657 |
| B | 5479 | 2058 | 1513912 |
| C | 6370 | 6410 | 1523811 |

TABLE 7

| Assay | 2 min RLU | 4 min RLU | Integrated RLU |
| --- | --- | --- | --- |
| A | 14284 | >9999 | 3369241 |
| B | 2089 | 1054 | 680056 |
| C | 13978 | 252 | 1818469 |

In the case of Assay C, the signal reagent is depleted before 4 min; this observation demonstrates that the HRP is leaching from the sol-gel since the time taken to deplete the signal reagent is longer for the HRP sol-gel+liquid signal than for the wash water from the HRP sol-gel+liquid signal.

The results clearly demonstrate that a primary object of the invention was achieved. The four components of the Aquanox water testing assay (HRP, luminol/p-iodophenol and sodium perborate) were successfully encapsulated into TMOS sol-gels and these gels, once dried, were active on the addition of deionised water.

The pellets demonstrated leaching of their enzyme or signal reagent components on addition of water within the 4 minute timescale of the Aquanox assay (see FIGS. 2 and 4) at the higher ratios of TMOS:$H_2O$. The results for the lower ratios, i.e. 3:2, 1:1 and 1:2, were dramatically different, showing very little leaching of the enzyme, and certainly insufficient to perform the Aquanox reaction. This effect was demonstrated whether the wash water of these pellets was assayed with liquid signal (see FIG. 2) or whether the pellets themselves were present in the cuvette (see FIG. 3).

It should be noted that the ratio of TMOS:solvent reported for standard mixtures in EP-A-0439318 was approx. 2:3 for sol-gel shapes, and 1:8 for thin-films; very little leachability was detected in the above results, at such low TMOS:$H_2O$ ratios. In describing the preparation of sol-gel immobilised enzymes, EP-A-0439318 reports that, after water washing of the gel, no significant enzyme activity was detected in the eluates. The method was based on chemical interaction of reagent(s) trapped in sol-gel glass which could interact with diffusible components.

The addition of a high molecular weight component, e.g. above 5,000 mw, enables less HRP to be added to the gels to achieve equivalent RLU values; see FIGS. 3 (ratio 5:2 curve at 1 mg/ml) and 7 and 8 (equivalent or higher signals with 0.75 mg/ml or 1 mg/ml). Such additives enable a reduction of up to 50% HRP in the gels, to achieve the required RLU values.

Both HRP and signal components obviously leached out of their respective pellets, as assays of the wash-water fractions demonstrated. Those assays containing both HRP and signal components in sol-gel pellets also demonstrated good activity, presumably based on the interactions of the components once they had leached out of the respective gels (see FIGS. 7 and 8). The sol-gels could successfully replace the liquid signal and enzyme reagents in control Aquanox assays (see FIGS. 3, 5 and 6), producing RLU values of the magnitude required and also, with further pore size manipulation, the required constant rate of light emission.

These results demonstrate the effectiveness of a solid, ready-to-use chemiluminescent reagent which, once deposited into test cuvettes, requires only one pipetting step, the addition of the water sample, thus simplifying the procedure and offering advantages over the existing system in the field. The cuvettes may be supplied, for use in an existing Aquanox machine, with the sol-gel pellets predispensed.

Improved results may be obtained by further optimisation of the pore size of the gel. Leaching may be enhanced by manipulation of the additives and TMOS ratio. In particular, varying the ratio of components will allow control over the rate of release. Another relevant factor is the size of particles; crushing provides modification in the context of curve B in FIG. 7.

If desired, the four components that are provided separately, in the Examples, may be combined into a reduced number of sol-gels, thus simplifying production. The sol-gels may be produced as thin films which may be layered on to the base/sides of the cuvettes. It will be evident that the solid chemiluminescent reagent is not limited to use in the particular water quality testing system that is illustrated, and that it is applicable to other assay systems employing such a chemiluminescent reaction.

What is claimed is:

1. A dried sol-gel containing a reactant that is released from said dried sol-gel in the presence of a liquid comprising water, wherein the dried sol-gel containing said reactant is obtained by reaction in the presence of said reactant of a solvent, comprising water, with at least 2 parts of tetramethoxysilane (TMOS) per part by volume solvent, and drying the resultant sol-gel containing said reactant.

2. A dried sol-gel according to claim 1, wherein the reactant is an oxidant or a reductant.

3. A dried sol-gel according to claim 2, wherein the reactant is luminol.

4. A dried sol-gel according to claim 2, further comprising horseradish peroxidase and an enhancer.

5. A dried sol-gel according to claim 1, wherein the reaction comprises 2.5 to 5 parts tetramethoxysilane (TMOS) per part solvent.

6. A dried sol-gel according to claim 1, said solvent consisting essentially of water.

7. A combination of first and second reactants that give a signal when mixed in the presence of an analyte in a liquid sample comprising water, wherein the reactants are separately contained in dried sol-gels that release the reactants in the presence of the liquid sample comprising water, and wherein said dried sol-gels containing said reactants are obtained by reaction in the presence of said reatants of a solvent, comprising water, with at least 2 parts of tetramethoxysilane (TMOS) per part by volume solvent, and drying the resultant sol-gels containing said reactants.

8. A combination according to claim 7, wherein the first and second reactants respectively comprise an oxidant and a reductant, and the reaction provides a detectable signal.

9. A combination according to claim 8, wherein the reductant is luminol, and the combination additionally comprises horseradish peroxidase and an enhancer contained in the same or separate dried sol-gels.

10. A combination according to claim 7, wherein the reaction comprises 2.5 to 5 parts tetramethoxysilane (TMOS) per part solvent.

11. A combination according to claim 7, said solvent consisting essentially of water.

12. A combination according to claim 11, wherein the first and second reactants respectively comprise an oxidant and a reductant, and the reaction provides a detectable signal.

13. A combination according to claim 11, wherein the reaction comprises 2.5 to 5 parts tetramethoxysilane (TMOS) per part solvent.

14. An analyte assay method, comprising:

combining first and second dried sol-gels containing reactants with an analyte in a liquid comprising water to form a combination, wherein said first and second dried sol-gels are obtained by reaction in the presence of said reactants of a solvent, comprising water, with at least 2 parts of tetramethoxysilane (TMOS) per part by volume solvent, and drying the resultant first and second sol-gels containing said reactants, wherein said first and second dried sol-gels release said reactants in the presence of the liquid comprising water, and wherein said reactants react to provide a detectable signal; and detecting for said detectable signal.

15. The analyte assay method of claim 14, wherein said first dried sol-gel contains a reductant and said second dried sol-gel contains an oxidant.

16. The analyte assay method of claim 15, wherein said reductant is luminol.

17. The analyte assay method of claim 15, wherein said combination further comprises horseradish peroxidase and an enhancer.

18. The analyte assay method of claim 14, wherein the ratio of tetramethoxysilane to solvent is from 2.5 to 1 to 5 to 1.

* * * * *